United States Patent [19]

Mitsuhashi et al.

[11] Patent Number: 4,528,188
[45] Date of Patent: Jul. 9, 1985

[54] POLYSACCHARIDE PS-A OBTAINED FROM BARRENWORT DERIVING FROM PLANTS BELONGING TO THE GENUS EPIMEDIUM, PROCESS FOR PREPARATION THEREOF AND PHYLACTIC AND IMMUNOSTIMULATING AGENTS COMPRISING SAID POLYSACCHARIDE PS-A EFFECTIVE COMPONENT

[75] Inventors: Susumu Mitsuhashi; Muneaki Takase; Sosuke Yasui, all of Tokyo; Ichiro Washizawa, Gunma; Kimitomo Yoshioka, Tokyo, all of Japan

[73] Assignee: Zenyaku Kogyo Kabushiki Kaisha, Tokyo, Japan

[21] Appl. No.: 456,027

[22] PCT Filed: Apr. 20, 1982

[86] PCT No.: PCT/JP82/00132
 § 371 Date: Dec. 28, 1982
 § 102(e) Date: Dec. 28, 1982

[87] PCT Pub. No.: WO82/03771
 PCT Pub. Date: Nov. 11, 1982

[30] Foreign Application Priority Data

Apr. 30, 1981 [JP] Japan .................................. 56-65892
Apr. 30, 1981 [JP] Japan .................................. 56-65893
Nov. 27, 1981 [JP] Japan ................................ 56-190202
Mar. 15, 1982 [JP] Japan .................................. 57-40438

[51] Int. Cl.$^3$ ..................... A61K 31/715; C08B 37/00
[52] U.S. Cl. ..................... 424/116; 536/1.1; 536/123; 514/54
[58] Field of Search ............... 424/116, 180; 536/1.1, 536/123

[56] References Cited

U.S. PATENT DOCUMENTS 4,163,780  8/1979  Ishida et al. ........................... 424/116
4,229,440 10/1980  Murofushi et al. ................... 536/123
4,409,385 10/1983  Nakajima et al. ..................... 536/123

Primary Examiner—Johnnie R. Brown
Attorney, Agent, or Firm—Scrivener Clarke Scrivener and Johnson

[57] ABSTRACT

A polysaccharide PS-A obtained from plants belonging to the genus Epimedium and having the following physicochemical properties, a process for preparation thereof and use as phylactic and immunostimulating agents comprising the polysaccharide PS-A as an effective component:

1. Elementary analysis: C=40.92; H=6.17; Ash=very small;
2. Molecular weight: 75,000±25,000 (average molecular weight);
3. Decomposition point: 205° C.;
4. pH: 7.0 (solution of 100 mg of PS-A in 50 ml of water);
5. Specific rotatory power: $[\alpha]_D^{19} = -23.6°$ (in H$_2$O, c=0.527);
6. Infrared absorption spectrum: $\nu_{max}^{KBr}$(cm$^{-1}$)/3400, 2900, 1620, 1400, 1230, 1060;
7. Ultraviolet absorption spectrum: Maximum absorption is not recognized in the range of 240–400 nm.;
8. Outward form: White or faint brown, amorphous powder;
9. Solubility:
   (a) Soluble in water;
   (b) Insoluble in methanol, ethanol, acetone, ethyl acetate, diethyl ether, hexane and chloroform;
10. Color reactions:
    Positive to the following reactions: (a) anthrone-sulfuric acid reaction; (b) Molisch's reaction; (c) skatol reaction; and (d) Bial's reaction;
    Negative to the following reactions: (a) ninhydrin reaction; (b) 2,4-DNP reaction; (c) Selivanoff's reaction; (d) naphthoresorcinol reaction; and (e) carbazol-sulfuric acid reaction;
11. Component sugars: Arabinose and galactose;
12. Homogeneity: Homogeneity is proved according to ultracentrifugation, electrophoresis and gel filtration.

5 Claims, 7 Drawing Figures

POLYSACCHARIDE PS-A OBTAINED FROM BARRENWORT DERIVING FROM PLANTS BELONGING TO THE GENUS EPIMEDIUM, PROCESS FOR PREPARATION THEREOF AND PHYLACTIC AND IMMUNOSTIMULATING AGENTS COMPRISING SAID POLYSACCHARIDE PS-A EFFECTIVE COMPONENT

TECHNICAL FIELD

The present invention relates to a polysaccharide (named PS-A) obtained from barrenwort deriving from plants belonging to the genus Epimedium of the family Berberidaceae and having the following physicochemical properties, a process for preparation thereof, and an agent of nonspecific resistance against infection (hereinafter referred to as a phylactic agent) and an immunostimulating agent comprising polysaccharide PS-A as an effective component:

1. Elementary analysis: C=40.92, H=6.17, Ash=very small;
2. Molecular weight: 75,000±25,000 (average molecular weight);
3. Decomposition point: 205° C.;
4. pH: 7.0 (solution of 100 mg of PS-A in 50 ml of water);
5. Specific rotatory power: $[\alpha]_D^{19} = -23.6°$ (in $H_2O$, c=0.527);
6. Infrared absoption spectrum: $\nu_{max}^{KBr}(cm^{-1})/3400$, 2900, 1620, 1400 1230, 1060;
7. Ultraviolet absorption spectrum: Maximum absorption is not recognized in the range of 240–400 nm.;
8. Outward form: White or faint brown, amorphous powder;
9. Solubility:
   (a) Soluble in water;
   (b) Insoluble in methanol, ethanol, acetone, ethyl acetate, diethyl ether, hexane or chloroform;
10. Color reactions:
    Positive to the following reactions: (a) anthrone-sulfuric acid reaction; (b) Molisch's reaction; (c) skatol reaction; and (d) Bial's reaction;
    Negative to the following reactions: (a) ninhydrin reaction; (b) 2,4-DNP reaction; (c) Selivanoff's reaction; (d) naphthoresorcinol reaction; and (e) carbazol-sulfuric acid reaction;
11. Component sugars: Arabinose and galactose;
12. Homogeneity: Homgeneity is proved according to ultracentrifugation, electrophoresis and gel filtration.

BACKGROUND ART

As the barrenwort deriving from plants belonging to the genus Epimedium, there are known *Epimedium macranthum*, M. et. D. var. *violaceum*, Fr., *Epimedium sagittatum*, Bak., *Epimedium macranthum*, M. et. D., *Epimedium koreanum*, Nak., etc. These plants are perennial herbs growing naturally in Japan, China and Korea, etc. The barrenwort is a crude drug obtained from a single species or a mixture of two or more of species belonging to the genus Epimedium by cutting down the plants at roots in June or July and drying them in the shade under good ventilation while keeping out rain and dew. The plants belonging to the genus Epimedium are perennials belonging to the family Berberidaceae, having the height of 30 to 60 cm and growing wild in fields and mountains in Japan, China, Korea or the like. The barrenwort marketed in Japan and Korea derives from *Epimedium macranthum*, M. et D. var. *violaceum*, Fr. or *Epimedium koreanum* Nak.; the barrenwort marketed in China, from *Epimedium sagittatum* Bak. or *Epimedium koreanum* Nak. In the field of Chinese medicines, herb of any plants belonging to the genus Epimedium is called "Yinyanghuo" irrespective of species of the plants and is infused and used as a cordial or tonic medicine. Components of this barrenwort have been studied from old and reports have been published. For example, by Akai et al. [Yakugaku Zasshi, 55, 537, 705, 719, 788 and 1139 (1935)] and Tomita et al. [Yakugaku Zasshi, 77, 114 and 212 (1957)], the substance called Icariin and the substances caled Des-O-methyl Icariin and Magnoflorine were found and the chemical structures of the respective substances have been determined. As to the phamacological characteristics, it has been reported for example by Maeda [Tokio Izi Sinsi, No. 2795, 2133 (1932)], Miyake [Okayama Igakkai Zasshi, 49, (10) 2043 (1937 )] and Hirashima et al. [Clinical Report, 4, 139 (1970)] that an extract from the barrenwort has the sperm-excitosecretory effect the hypotensive effect and the blood sugar descending effect. But their details are still unclear in many points.

We made researches on this barrenwort and succeeded in obtaining an extract having an immunostimulating activity by extracting plants belonging to the genus Epimedium. Japanese patent applications Nos. 21152/1980, 57424/1980 and 83539/1980 were filed on the basis of this finding. We further made researches to succeed in extraction and isolation of the polysaccharide PS-A, as shown in the following flow chart, having an phylactic activity and an immunostimulating activity. We have now completed the present invention based on this success.

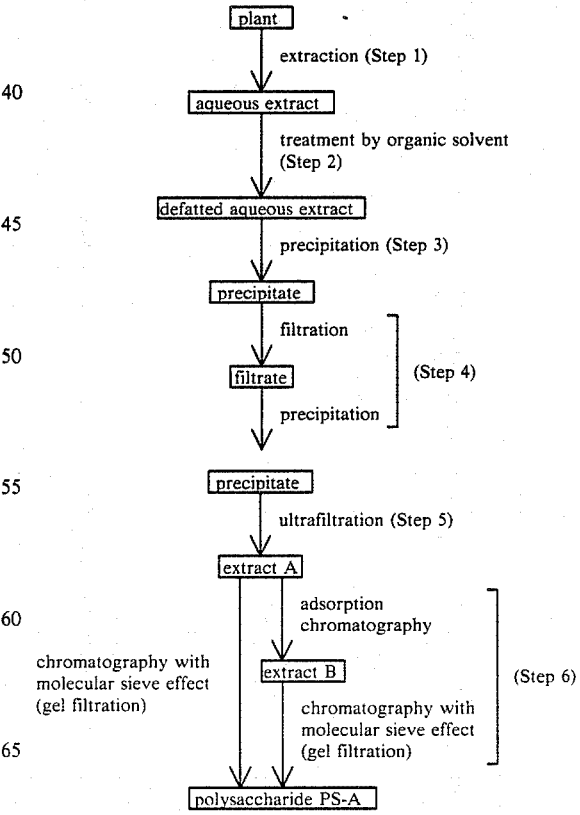

DISCLOSURE OF THE INVENTION

First of all, extraction, isolation and purification of polysaccharide PS-A will be described.

Step 1

A barrenwort deriving from plants belonging to the genus Epimedium is extracted with a mixed solvent of water and a water-miscible organic solvent or with water, and the obtained extract is concentrated under reduced pressure. As the water-miscible organic solvent there can be used, for example, lower alcohols such as methanol, ethanol and isopropanol, ketones such as acetone and water-miscible ethers such as dioxane and the like. A mixture of two or more of these water-miscible solvents may also be used. Furthermore, lower aliphatic acids such as acetic acid having a concentration lower than 1 normality, water-miscible lower amines such as ethanol amine having a concentration lower that 1 mol/l can be used as the extraction solvent. In view of the concentration opration, it is preferred that the operation of obtainig the intended aqueous extract be carried out by using a mixed solvent of a water-miscible organic solvent and water and that the amount of the organic solvent be smaller than 50% by volume. In the present invention, herb of barrenwort commercially available in Japan, China or the like may be used as it is, but it is preferred that it be used after it has been finely divided into pieces.

Step 2

The so obtained aqueous extract is then treated by an organic solvent or solvents.

This operation is accomplished by adding one or more organic solvents selected from lower aliphatic esters such as ethyl acetate, halogenated hydrocarbons such as chloroform, hardly water-soluble ethers such as diethyl ether and aliphatic hydrocarbons such as n-hexane and the like, sufficiently shaking the mixture and collecting the aqueous layer alone. The obtained aqueous layer is subjected to the same operation 3 to 5 times and is heated on a water bath to remove the organic solvent left in a small amount, and then filtered to obtain an aqueous extract treated by the organic solvent or solvents. There may be adopted a method in which Step 2 is first conducted and Step 1 is then carried out.

Step 3

A water-soluble organic solvent is added to the aqueous extract obtained in step 2 to effect the precipitation. The formed precipitate is recovered by filtration and is washed with a water-soluble organic solvent. The washed precipitate is poured into water. Then, a water-soluble organic solvet is added to the solution to effect the precipitation again. The formed precipitate is recovered by filtration and dried under reduced pressure to obtain an extract. As the water-soluble organic solvent, there may be used, for example, lower alcohols such as methanol and ethanol and ketones such as acetone and the like. A mixture of two or more of these organic solvents may also be used. The so obtained precipitate may be purified by extraction with water. More specifically, the precipitate is mixed with water at room temperature, and the mixture is sufficiently stirred and is then filtered. The filtrate is concentrated to dryness under reduced pressure for purification.

Step 4

The precipitate obtained in Step 3 is dissolved in water and then a long-chained quaternary ammonium salt is added thereto to remove a resultant complex.

One example of the operation will be now described.

The precipitate obtained in Step 3 is dissolved in an inorganic salt aqueous solution whose amount is 50 to 80 times (V/W) that of the precipitate. It is preferred that the inorganic salt aqueous solution be 0.01 to 0.05 mol/l of aqueous solution of sodium sulfate or sodium chloride. Then a long-chained quaternary ammonium salt such as cetyltrimethylammonium salt or cetylpyridinium salt is added to the solution in an amount 0.5 to 3 times (W/W) that of the precipitate obtained in Step 3. The resultant precipitate is removed by filtration or centrifugation. A water-soluble organic solvent is added to the recovered filtrate in an amount more than 3 times (V/V) that of the filtrate and resultant precipitate is recovered by filtration.

Step 5

The precipitate obtained in Step 3 is dissolved in water and then low molecular substances are removed therefrom.

One example of the operation will be now described.

Water is added to the precipitate obtained in Step 4 in an amount 300 to 400 times (V/W) that of the precipitate and the mixture is adequately stirred under heating at 35° to 45° C. for dissolution. The solution is ultrafiltered through a membrane with nominal molecular weight ultrafiltration value of 1,000 to remove the substances passing through the filtering membrane. Water is added to the condensate caught by the membrane in an amount of 5 to 10 times (V/V) that of the condensate and the mixture is adequately stirred, diluted and ultrafiltered again. This operation is repeated a few times to completely remove the substances passing through the membrane. The condensate caught by the membrane is recovered, and water is added for dilution to the recovered condensate in an amount of 2 to 5 times (V/V) that of the condensate. Then, a water-soluble organic solvent is added to the solution in an amount of more than 4 times (V/V) that of the solution to obtain extract A as precipitate.

Step 6

The intended polysaccharide PS-A can be obtained by subjecting extract A to chromatography. In the chromatography, a carrier having a molecular sieve effect may be used. Before this chromatography, chromatography with an adsorbent may be effected.

The operation will be shown below concretely.

Extract A is dissolved in water and the solution is subjected to the chromatography using a carrier having a molecular sieve effect such as gel filtration. A fraction shown as Fr-1 in FIG. 1 is collected to obtain the polysaccharide PS-A of the present invention. Polysaccharides (named PS-B and PS-C) are also obtained from fractions Fr-2 and Fr-3, respectively, in FIG. 1.

The following operation may be effected for the purpose of obtaining the polysaccharides of high purities:

Extract A is subjected to adsorption chromatography. After the elution with water, the eluted fraction is separated out. (Polysaccharide PS-B is obtained by concentrating this fraction to dryness under reduced pressure.) As the adsorbent used in this step, there may be mentioned, for example, a polyamide resin or an anion-exchange resin. The polyamide resin is preferred. Then, the elution is continued by using a volatile, weakly alkaline aqueous solution such as aqueous ammonia solution as the elution solvent. The eluted fraction is taken and concentrated to dryness under reduced pressure or freeze-dried to obtain extract B.

Extract B is dissolved in water and the solution is subjected to chromatography using a carrier having a molecular sieve effect such as gel filtration. A fraction eluted out first is taken to obtain polysaccharide PS-A. (PS-C can be obtained from the remaining fraction.)

The polysaccharide PS-A has the following physicochemical properties:

1. Elementary analysis: C=40.92; H=6.17; Ash=very small;
2. Molecular weight: 75,000±25,000 (average molecular weight);

It was measured according to the method reported in P. Andrews, Methods of Biochemical Analysis, ed. by D. Glick, John Wiley & Sons, Inc., New York, 18 2 (1970). The filler used was Sephadex G-200 (produced by Pharmacia Fine Chemical Co., Ltd., Sweden). The column used had 2.5 mm in diameter and 100 cm in length. The elusion liquid used was 0.1 mol aqueous sodium chloride solution at a rate of 10 ml/hour. Standards used for determining calibration curves were Dextran T-500 ($\overline{M.W.}$ 487,000), Dextran T-70 ($\overline{M.W.}$ 70,300) and Dextran T-40 ($\overline{M.W.}$ 39,000) (produced by Pharmacia Fine Chemical Co., Ltd., Sweden).

3. Decomposition point: 205° C.;
4. pH: 7.0 (solution of 100 mg of PS-A in 50 ml of water);
5. Specific rotatory power: $[\alpha]_D^{19} = -23.6°$ (in $H_2O$, c=0.527);
6. Infrared absorption spectrum: $\nu_{max}^{KBr}(cm^{-1})/3400$, 2900, 1620, 1400 1230, 1060;
7. Ultraviolet absorption spectrum: Maximum absorption is not recognized in the range of 240–400 nm.;
8. Outward form: White or faint brown, amorphous powder;
9. Solubility:
    (a) Soluble in water;
    (b) Insoluble in methanol, ethanol, acetone, ethyl acetate, diethyl ether, hexane or chloroform;
10. Color reactions:
    Positive to the following reactions: (a) anthrone-sulfuric acid reaction; (b) Molisch's reaction; (c) skatol reaction; and (d) Bial's reaction;
    Negative to the following reactions: (a) ninhydrin reaction; (b) 2,4-DNP reaction; (c) Selivanoff's reaction; (d) naphthoresorcinol reaction; and (e) carbazol-sulfuric acid reaction;
11. Component sugars:
    5 ml of 1N-sulfuric acid is added to 20 mg of the polysaccharide PS-A and the mixture is refluxed at 100° C. for 2 hours; after cooling, it is neutralized with barium hydroxide; the precipitate formed is filtered out and the filtrate is subjected to paper chromatography to confirm the presence of arabinose and galactose;
12. Homogeneity:
    (a) Ultracentrifugation: Homogeneity is proved by the equilibrium density-gradient centrifugation (120,000 G×72 hours, $CaCl_2$);
    (b) Electrophoresis: Homogeneity is proved by the electrophoresis using a cellulose acetate membrane (20–25 V/cm, 2 hours);
    (c) Gel filtration: Homogeneity is proved by the gel filtration using Sephadex G-100.

The polysaccharides PS-B and PS-C have the following physicochemical properties:

| Item | PS-B | PS-C |
|---|---|---|
| 1. Elementary analysis | C = 37.69, H = 6.00 Ash = very small | C = 40.75, H = 6.28 Ash = very small |
| 2. Molecular weight (average molecular weight) | 50,000 ± 25,000 | 25,000 ± 15,000 |
| 3. Decomposition point | 200° C. | 175° C. |
| 4. pH | 6.9 | 7.0 |
| 5. Specific rotatory power | $[\alpha]_D^{19} = -0.5°$ (in $H_2O$, c = 0.756) | $[\alpha]_C^{19} = -12.6°$ (in $H_2O$, c = 0.512) |
| 6. Infrared absorption spectrum | See FIG. 3. $\nu_{max}^{KBr}(cm^{-1})/3350$, 2920, 1630, 1550 1420, 1100 | See FIG. 4. $\nu_{max}^{KBr}(cm^{-1})/3300\sim3400$, 2900, 1600, 1400, 1040~1060 |

As to the items 7. Ultraviolet absorption spectrum, 8. Outward form, 9. Solubility, 10. Color reactions, 11. Component sugars and 12. Homogeneity, the polysaccharides PS-B and PS-C have the same physicochemical properties as those of the polysaccharide PS-A.

Moreover, the extracts A and B have the following physicochemical properties:

| Item | Extract A | Extract B |
|---|---|---|
| 1. Outward form | Liver brown powder | Faint brown or brown powder |
| 2. pH | 7.0 | 7 0 |
| 3. Infrared absorption spectrum | See FIG. 5. $\nu_{max}^{KBr}(cm^{-1})/3400$, 2900, 1600, 1400, 1050 | See FIG. 6. $\nu_{max}^{KBr}(cm^{-1})/3200$ 1600, 1400, 1100 |
| 4. Ultraviolet absorption spectrum | Maximum absorption is not recognized in the range of 240–400 nm. | |
| 5. Solubility | (a) Soluble in water. (b) Insoluble in methanol, ethanol, acetone, ethyl acetate, diethyl ether, hexane or chloroform. | |
| 6. Color reaction | Positive to the following reactions: (a) anthrone-sulfuric acid reaction, (b) Molisch's reaction, (c) skatol reaction and (d) Bial's reaction. Negative to the following reactions: (a) ninhydrin reaction, (b) 2,4-DNP reaction, (c) Selivanoff's reaction, (d) naphthoresorcinol reaction and (e) carbazol-sulfuric acid reaction. | |
| 7. Component sugars | 5 ml of 1N—sulfuric acid is added to 20 mg of the extract A or B and the mixture is refluxed under heating for 2 hours. After cooling, it is neutralized with barium hydroxide. The precipitate formed is filtered and the filtrate is subjected to paper chromatography to confirm the presence of arabinose and galactose. | |

The following tests (I)–(III) were effected for confirming the utility of the above polysaccharide PS-A:

(I) TEST FOR JUDGING PHYLACTIC EFFECTS (1) Effects on subjects in normal state

A sample was administered subcutaneously to the back of each of 5-weeks-old male mice of the ICR/JCL strain having a body weight of about 25 g (each group consiting of 10 mice) once a day continuously for five days (5 times in total). Physiological saline solution (hereinafter referred to as PS) was given to a control group. On the sixth day, *E. coli* ML 4707 was challenged to each mouse by the intraperitoneal injection. The tests were carried out in the same manner as above using *Ps. aeruginosa* 70P II, *S. aureus* Smith diffuse, *K.* pneumoniae GN 6445, *S. enteritidis* 116-54 and *P. vulgaris* GN 5737. Seven days after the challenge, viable count was examined. The results are shown in Tables 1–6.

TABLE 1

Effects on *E. coli*

| bacterial challenge (cells/mouse) | | $1.0 \times 10^7$ | $3.2 \times 10^6$ | $1.0 \times 10^6$ |
|---|---|---|---|---|
| Viable count in control group (%) | | 0 | 30 | 60 |
| Viable count in polysaccharide PS-A-treated group (%) | 0.1 mg/kg body wt./day | 10 | 30 | 70 |
| | 0.5 mg/kg body wt./day | 20 | 40 | 100 |
| | 2.5 mg/kg body wt./day | 40 | 80 | 100 |
| Reference | | | | |
| Viable count in polysaccharide PS-B-treated group (%) | 0.5 mg/kg body wt./day | 10 | 20 | 40 |
| | 2.5 mg/kg body wt./day | 20 | 60 | 70 |
| | 12.5 mg/kg body wt./day | 40 | 80 | 80 |
| Viable count in polysaccharide PS-C-treated group (%) | 0.3 mg/kg body wt./day | 10 | 30 | 60 |
| | 1.5 mg/kg body wt./day | 20 | 40 | 70 |
| | 7.5 mg/kg body wt./day | 30 | 50 | 90 |
| Viable count in extract A-treated group (%) | 1.0 mg/kg body wt./day | 10 | 30 | 40 |
| | 5.0 mg/kg body wt./day | 20 | 40 | 60 |
| | 25.0 mg/kg body wt./day | 40 | 60 | 80 |
| Viable count in extract B-treated group (%) | 0.5 mg/kg body wt./day | 10 | 20 | 40 |
| | 2.5 mg/kg body wt./day | 20 | 40 | 50 |
| | 12.5 mg/kg body wt./day | 30 | 50 | 100 |

TABLE 2

Effects on *Ps. aeruginosa*

| Bacterial challenge (cells/mouse) | | $5.0 \times 10^7$ | $1.6 \times 10^7$ | $5.0 \times 10^6$ |
|---|---|---|---|---|
| Viable count in control group (%) | | 0 | 20 | 40 |
| Viable count in polysaccharide PS-A-treated group (%) | 0.1 mg/kg body wt./day | 20 | 20 | 70 |
| | 0.5 mg/kg body wt./day | 20 | 50 | 90 |
| | 2.5 mg/kg body wt./day | 30 | 50 | 100 |
| Reference | | | | |
| Viable count in polysaccharide PS-B-treated group (%) | 0.5 mg/kg body wt./day | 10 | 30 | 20 |
| | 2.5 mg/kg body wt./day | 20 | 30 | 60 |
| | 12.5 mg/kg body wt./day | 30 | 70 | 100 |
| Viable count in polysaccharide PS-C-treated group (%) | 0.3 mg/kg body wt./day | 10 | 30 | 30 |
| | 1.5 mg/kg body wt./day | 10 | 30 | 50 |
| | 7.5 mg/kg body wt./day | 30 | 50 | 100 |
| Viable count in extract A-treated group (%) | 1.0 mg/kg body wt./day | 0 | 20 | 20 |
| | 5.0 mg/kg body wt./day | 10 | 40 | 60 |
| | 25.0 mg/kg body wt./day | 30 | 50 | 80 |
| Viable count in extract B-treated group (%) | 0.5 mg/kg body wt./day | 10 | 10 | 30 |
| | 2.5 mg/kg body wt./day | 20 | 50 | 70 |
| | 12.5 mg/kg body wt./day | 30 | 50 | 80 |

TABLE 3

Effects on *S. aureus*

| Bacterial challenge (cells/mouse) | | $2.0 \times 10^9$ | $1.0 \times 10^9$ | $5.0 \times 10^8$ |
|---|---|---|---|---|
| Viable count in control group (%) | | 0 | 10 | 50 |
| Reference | | | | |
| Viable count in polysaccharide PS-A-treated group | 0.1 mg/kg body wt./day | 30 | 30 | 70 |
| | 0.5 mg/kg body wt./day | 40 | 50 | 70 |
| | 2.5 mg/kg body wt./day | 60 | 60 | 100 |
| Viable count in polysaccharide PS-B-treated group (%) | 0.5 mg/kg body wt./day | 10 | 30 | 60 |
| | 2.5 mg/kg body wt./day | 10 | 40 | 70 |
| | 12.5 mg/kg body wt./day | 20 | 40 | 90 |
| Viable count in polysaccharide PS-C-treated group (%) | 0.3 mg/kg body wt./day | 10 | 20 | 50 |
| | 1.5 mg/kg body wt./day | 10 | 30 | 80 |
| | 7.5 mg/kg body wt./day | 30 | 50 | 90 |
| Viable count in extract A-treated group (%) | 1.0 mg/kg body wt./day | 10 | 20 | 60 |
| | 5.0 mg/kg body wt./day | 10 | 40 | 70 |
| | 25.0 mg/kg body wt./day | 20 | 50 | 80 |
| Viable count in extract B-treated group (%) | 0.5 mg/kg body wt./day | 10 | 20 | 60 |
| | 2.5 mg/kg body wt./day | 20 | 40 | 70 |
| | 12.5 mg/kg body wt./day | 20 | 60 | 90 |

TABLE 4

Effects on *K. poneumoniae*

| Bacterial challenge (cells/mouse) | | $5.0 \times 10^7$ | $1.3 \times 10^7$ | $5.0 \times 10^6$ |
|---|---|---|---|---|
| Viable count in control group (%) | | 0 | 20 | 60 |
| Viable count in polysaccharide PS-A-treated group (%) | 0.1 mg/kg body wt./day | 10 | 40 | 90 |
| | 0.5 mg/kg body wt./day | 40 | 50 | 100 |
| | 2.5 mg/kg wt./day | 40 | 70 | 100 |
| Reference | | | | |
| Viable count in polysaccaride PS-B-treated group (%) | 0.5 mg/kg body wt./day | 10 | 30 | 60 |
| | 2.5 mg/kg body wt./day | 50 | 60 | 100 |
| | 12.5 mg/kg body wt./day | 60 | 80 | 100 |
| Viable count in polysaccharide PS-C-treated group (%) | 0.3 mg/kg body wt./day | 10 | 30 | 70 |
| | 1.5 mg/kg body wt./day | 30 | 40 | 90 |
| | 7.5 mg/kg body wt./day | 30 | 60 | 100 |
| Viable count in extract A-treated group (%) | 1.0 mg/kg body wt./day | 10 | 20 | 60 |
| | 5.0 mg/kg body wt./day | 30 | 40 | 80 |
| | 25.0 mg/kg body wt./day | 40 | 60 | 90 |
| Viable count in extract B-treated group (%) | 0.5 mg/kg body wt./day | 20 | 30 | 60 |
| | 2.5 mg/kg body wt./day | 40 | 50 | 90 |
| | 12.5 mg/kg body wt./day | 40 | 80 | 100 |

TABLE 5

Effect on S. enteritidis

| Bacterial challenge (cells/mouse) | | $1.0 \times 10^5$ | $1.0 \times 10^4$ | $1.0 \times 10^3$ |
|---|---|---|---|---|
| Viable count in Control group (%) | | 0 | 0 | 30 |
| Viable count in polysaccharide PS-A-treated group (%) | 0.1 mg/kg body wt./day | 10 | 20 | 60 |
| | 0.5 mg/kg body wt./day | 10 | 20 | 80 |
| | 2.0 mg/kg body wt./day | 20 | 20 | 90 |
| Reference | | | | |
| Viable count in polysaccharide PS-B-treated group (%) | 0.5 mg/kg body wt./day | 0 | 0 | 30 |
| | 2.5 mg/kg body wt./day | 0 | 0 | 40 |
| | 12.5 mg/kg body wt./day | 10 | 30 | 70 |
| Viable count in polysaccharide PS-C-treated group (%) | 0.3 mg/kg body wt./day | 0 | 0 | 30 |
| | 1.5 mg/kg body wt./day | 0 | 10 | 50 |
| | 7.5 mg/kg body wt./day | 10 | 30 | 60 |
| Viable count in extract A-treated group (%) | 1.0 mg/kg body wt./day | 0 | 0 | 30 |
| | 5.0 mg/kg body wt./day | 0 | 0 | 40 |
| | 25.0 mg/kg body wt./day | 10 | 30 | 50 |
| Viable count in extract B-treated group (%) | 0.5 mg/kg body wt./day | 0 | 0 | 30 |
| | 2.5 mg/kg body wt./day | 0 | 10 | 50 |
| | 12.5 mg/kg body wt./day | 10 | 30 | 60 |

Note
Fourteen days after the challenge, viable count was examined.

TABLE 6

Effects on P. vulgaris

| Bacterial challenge (cells/mouse) | | $5.0 \times 10^8$ | $1.3 \times 10^8$ | $5.0 \times 10^7$ |
|---|---|---|---|---|
| Viable count in control group (%) | | 0 | 10 | 10 |
| Viable count in polysaccharide PS-A-treatedd group (%) | 0.1 mg/kg body wt./day | 30 | 40 | 100 |
| | 0.5 mg/kg body wt./day | 30 | 50 | 90 |
| | 2.5 mg/kg body wt./day | 40 | 50 | 80 |
| Reference | | | | |
| Viable count in polysaccharide PS-B-treated group (%) | 0.5 mg/kg body wt./day | 20 | 30 | 80 |
| | 2.5 mg/kg body wt./day | 30 | 40 | 80 |
| | 12.5 mg/kg body wt./day | 30 | 40 | 100 |
| Viable count in polysaccharide PS-C-treated group (%) | 0.3 mg/kg body wt./day | 20 | 30 | 50 |
| | 1.5 mg/kg body wt./day | 20 | 40 | 70 |
| | 7.5 mg/kg body wt./day | 30 | 50 | 100 |
| Viable count in extract A-treated group (%) | 1.0 mg/kg body wt./day | 10 | 20 | 40 |
| | 5.0 mg/kg body wt./day | 20 | 30 | 50 |
| | 25.0 mg/kg body wt./day | 30 | 40 | 70 |
| Viable count in extract B-treated group (%) | 0.5 mg/kg body wt./day | 10 | 30 | 40 |
| | 2.5 mg/kg body wt./day | 20 | 30 | 50 |
| | 12.5 mg/kg body wt./day | 20 | 40 | 70 |

In the above tests, the phylactic effects of polysaccharides PS-A, PS-B nd PS-C, and extracts A and B on E. coli, Ps. aeruginosa, S. aureus, K. pneumoniae, S. enteritidis and P. vulgaris were recognized.

(2) Effect on subjects in the immunosuppressive state

A sample was administered subcutaneously to the back of each of 5-weeks-old female mice of the ICR/JCL strain having a body weight of about 25 g (each group consisting of 10 mice) once a day continuously for four days (4 times in total). PS was given to a control group. On the first day of the administration, cyclophosphamide (200 mg/kg body weight) was injected thereto by the intraperitoneal injection. On the next day of the final administration (i.e. on the fifth day), E. coli ML 4707 was challenged to each mouse by the intraperitoneal injection. The tests were carried out in the same manner as above using Ps. aeruginosa 70P II, S. aureus Smith diffuse, and P. vulgaris GN 5737. Seven days after the challenge, viable count was examined. The results are shown in Tables 7–10.

TABLE 7

Effects on E. coli in the immunosuppressive state

| Biological challenge (cells/mouse) | | $1.0 \times 10^6$ | $5.0 \times 10^5$ |
|---|---|---|---|
| Viable count in control group (%) | | 0 | 20 |
| Viable count in polysaccharide PS-A-treated group (%) | 0.2 mg/kg body wt./day | 50 | 70 |
| | 1.0 mg/kg body wt./day | 100 | 100 |
| Reference | | | |
| Viable count in polysaccharide PS-B-treated group (%) | 1.0 mg/kg body wt./day | 30 | 50 |
| | 5.0 mg/kg body wt./day | 70 | 80 |
| Viable count in polysaccharide PS-C-treated group (%) | 0.6 mg/kg body wt./day | 40 | 50 |
| | 3.0 mg/kg body wt./day | 60 | 70 |
| Viable count in extract A-treated group (%) | 2.0 mg/kg body wt./day | 30 | 50 |
| | 10.0 mg/kg body wt./day | 60 | 70 |
| Viable count in extract B-treated group (%) | 1.0 mg/kg body wt./day | 40 | 50 |
| | 5.0 mg/kg body wt./day | 60 | 70 |

TABLE 8

Effects on Ps. aeruginosa immunosuppressive state

| Biological challenge (cells/mouse) | | $2.0 \times 10^6$ | $5.0 \times 10^5$ |
|---|---|---|---|
| Viable count in control group (%) | | 0 | 30 |
| Viable count in polysaccharide PS-A-treated group (%) | 0.2 mg/kg body wt./day | 30 | 80 |
| | 1.0 mg/kg body wt./day | 70 | 100 |
| Reference | | | |
| Viable count in polysaccharide PS-B-treated group (%) | 1.0 mg/kg body wt./day | 20 | 50 |
| | 5.0 mg/kg body wt./day | 70 | 90 |
| Viable count in polysaccharide PS-C-treated group (%) | 0.6 mg/kg body wt./day | 30 | 50 |
| | 3.0 mg/kg body wt./day | 60 | 80 |
| Viable count in extract A-treated group (%) | 2.0 mg/kg body wt./day | 10 | 30 |
| | 10.0 mg/kg body wt./day | 50 | 60 |
| Viable count in extract B-treated group (%) | 1.0 mg/kg body wt./day | 20 | 40 |
| | 5.0 mg/kg body wt./day | 50 | 70 |

TABLE 9

Effects on *S. aureus* in the immunosuppressive state

| Biological challenge (cells/mouse) | | $5.0 \times 10^7$ | $5.0 \times 10^6$ |
|---|---|---|---|
| Viable count in control group (%) | | 20 | 40 |
| Viable count in polysaccharide PS-A-treated group (%) | 0.2 mg/kg body wt./day | 90 | 100 |
| | 1.0 mg/kg body wt./day | 100 | 100 |
| Reference | | | |
| Viable count in polysaccharide PS-B-treated group (%) | 1.0 mg/kg body wt./day | 50 | 70 |
| | 5.0 mg/kg body wt./day | 100 | 100 |
| Viable count in polysaccharide PS-C-treated group (%) | 0.6 mg/kg body wt./day | 50 | 70 |
| | 3.0 mg/kg body wt./day | 90 | 100 |
| Viable count in extract A-treated group (%) | 2.0 mg/kg body wt./day | 40 | 70 |
| | 10.0 mg/kg body wt./day | 80 | 90 |
| Viable count in extract B-treated group (%) | 1.0 mg/kg body wt./day | 50 | 70 |
| | 5.0 mg/kg body wt./day | 70 | 90 |

TABLE 10

Effects on *P. vulgaris* in the immunosuppressive state

| Biological challenge (cells/mouse) | | $1.0 \times 10^7$ | $2.0 \times 10^6$ |
|---|---|---|---|
| Viable count in control group (%) | | 0 | 30 |
| Viable count in polysaccharide PS-A-treated group (%) | 0.2 mg/kg body wt./day | 20 | 100 |
| | 1.0 mg/kg body wt./day | 70 | 100 |
| Reference | | | |
| Viable count in polysaccharide PS-B-treated group (%) | 1.0 mg/kg body wt./day | 20 | 60 |
| | 5.0 mg/kg body wt./day | 60 | 80 |
| Viable count in polysaccharide PS-C-treated group (%) | 0.6 mg/kg body wt./day | 10 | 50 |
| | 3.0 mg/kg body wt./day | 50 | 70 |
| Viable count in extract A-treated group (%) | 2.0 mg/kg body wt./day | 10 | 40 |
| | 10.0 mg/kg body wt./day | 40 | 60 |
| Viable count in extract B-treated group (%) | 1.0 mg/kg body wt./day | 10 | 50 |
| | 5.0 mg/kg body wt./day | 50 | 80 |

Polysaccharide PS-A, PS-B and PS-C and extracts A and B exhibited the phyractic effects on *E. coli*, *Ps. aeruginosa*, *S. aureus* and *P. vulgaris* even in the immunosuppressive state.

(3) Combination with antibiotics

A sample was administered subcutaneously to the back of each of 5-weeks-old male mice of the ICR/JCL strain having a body weight of about 25 g (each group consisting of 10 mice) once a day continuously for five days (5 times in total). PS was given to a control group. On the sixth day, $1.0 \times 10^7$ cells of *E. coli* ML 4707 was challenged thereto by the intraperitoneal injection. 12.5 mg/kg of ampicillin (Ampicillin sodium for injection; produced by Toyama Kagaku Co., Ltd., Japan) was administered to each mouse twice (directly after the intraperitoneal injection and 4 hours thereafter). Seven days after the challenge, viable count was examined. The results are shown in Table 11.

TABLE 11

Effects obtained by the combination with antibiotics

| Item | Viable count (%) |
|---|---|
| Control group | 0 |
| Group treated with only ampicillin | 20 |
| Group treated with polysaccharide PS-A (0.1 mg/kg body wt./day) | 10 |
| Group treated with polysaccharide PS-A (0.1 mg/kg body wt./day) + ampicillin | 100 |
| Reference | |
| Group treated with polysaccharide PS-B (0.5 mg/kg body wt./day) | 0 |
| Group treated with polysaccharide PS-B (0.5 mg/kg body wt./day) + ampicillin | 50 |
| Group treated with polysaccharide PS-C (0.3 mg/kg body wt./day) | 0 |
| Group treated with polysaccharide PS-C (0.3 mg/kg body wt./day) + ampicillin | 50 |
| Group treated with extract A (1.0 mg/kg body wt./day) | 0 |
| Group treated with extract A (1.0 mg/kg body wt./day) + ampicillin | 30 |
| Group treated with extract B (0.5 mg/kg body wt./day) | 0 |
| Group treated with extract B (0.5 mg/kg body wt./day) + ampicillin | 40 |

Polysaccharides PS-A, PS-B and PS-C, extracts A and B exhibited their combined effect when they were used in combination with the antibiotic.

(4) Effects used in combination with an antibiotic on subjects in the immunosuppressive state A sample was administered subcutaneously to the back of each of 5-weeks-old female mice of the ICR/JCL strain having a body weight of about 25 g (each group consisting of 10 mice) once a day continuously for four days (4 times in total). PS was given to a control group. On the first day, 200 mg/kg of cyclophosphamide was injected to them by the intraperitoneal injection. On the next day of the final administration (i.e. on the fifth day), $1.0 \times 10^6$ cells of *E. coli* ML 4707 was challenged thereto by the intraperitoneal injection. One hour thereafter, 6.25 mg/kg of ampicillin (Ampicillin-sodium for injection; produced by Toyama Kagaku Co., Ltd., Japan) was administered to the back of each mouse by the subcutaneous injection. Seven days after the challenge, viable count was examined. The results are shown in Table 12.

TABLE 12

Effects obtained by the combination with antibiotics on subjects in the immunosuppressive state

| Item | Viable count (%) |
|---|---|
| Control group | 0 |
| Group treated with only ampicillin | 10 |
| Group treated with polysaccharide PS-A (0.1 mg/kg body wt./day) | 0 |
| Group treated with polysaccharide PS-A (0.1 mg/kg body wt./day) + ampicillin | 100 |
| Reference | |
| Group treated with polysaccharide PS-B (0.5 mg/kg body wt./day) | 0 |
| Group treated with polysaccharide PS-B (0.5 mg/kg body wt./day) + ampicillin | 40 |
| Group treated with polysaccharide PS-C (0.3 mg/kg body wt./day) | 0 |
| Group treated with polysaccharide PS-C (0.3 mg/kg body wt./day) + ampicillin | 50 |
| Group treated with extract A (1.0 mg/kg body wt./day) | 0 |
| Group treated with extract A (1.0 mg/kg body wt./day) + ampicillin | 30 |
| Group treated with extract B | 0 |

TABLE 12-continued

Effects obtained by the combination with antibiotics on subjects in the immunosuppressive state

| Item | Viable count (%) |
|---|---|
| (0.5 mg/kg body wt./day) | |
| Group treated with extract B (0.5 mg/kg body wt./day) + ampicillin | 30 |

Polysaccharides PS-A, PS-B nd PS-C and extracts A and B exhibited their combined effects when they were used in combination with the antibiotic even in the immunosuppressive state.

It is apparent from the above phylaxios tests (1)-(4) that all of the polysaccharides PS-A, PS-B and PS-C and extracts A and B have the phylactic effects.

Amoung them, polysaccharide PS-A has particularly excellent phylactic effects.

(II) Test for judging immunostimulating effects (1) Macrophage phagocytic function test ① Reticuloendothelial function test:

A sample was administered into the intraperitoneal injection of 7-weeks-old male mice of the ICR/JCL strain having a body weight of about 30 g (each group consisting of 5 mice) once a day continuously for five days (5 times in total). Phosphate buffered physiological saline solution (hereinafter referred to as "PBS") was given to a control group.

In order to examine influences on the phagocytosis in the reticuloendothelial system, colloidal carbon (Pelikan Drawing Ink 17 Black produced by Günther Wagner Co., Ltd., West Germany) was injected into tail veins of the respective mice of the treated group and control group after passage of 24 hours from the last treatment, and the clearance from blood was examined according to the following procedures. More specifically, colloidal carbon was diluted with a physiological saline solution containing 3% of gelatin so that the carbon concentration was reduced to ½ and the dilution was injected into the tail vein at a rate of 10 ml/kg body weight. Then, 0.010 ml of blood was collected by a heparin-treated micropppipette according to the eyepit puncture method and immediately transferred into 2 ml of 0.1% $Na_2CO_3$ to dissolve the blood. The absorbance at 650 nm was mesured by Hitachi Double Beam Model 124 (supplied by Hitachi Co., Ltd., Japan). The phagocytic index was determined by injecting the colloidal carbon dilution into the vein, collecting blood after passage of 2 minutes ($t_1$) and 20 minutes ($t_2$) and performing calculation based on the carbon concentrations ($C_1$ and $C_2$: after passage of 2 minutes and 20 minutes, respectively) in samples bloods according to the following formulae:

$$\text{Phagocytic index: } K_2^{20} = \frac{(\log C_1) - (\log C_2)}{t_2 - t_1}$$

$$\text{Half-value period in blood: } T_{\frac{1}{2}} = \frac{0.301}{K_2^{20}}$$

The obtained results are shown in Table 13.

TABLE 13

Results of reticuloendothelial function test

| Item | Dose | $K_2^{20}$ | $T\frac{1}{2}$ (min.) |
|---|---|---|---|
| polysaccharide PS-A-treated group | 0.47 mg | 0.0192 ± 0.0055 | 16.70 ± 4.43 |
| Control group | | 0.0192 ± 0.0021 | 34.52 ± 9.82 |
| Reference Polysaccharide PS-B-treated group | 0.72 mg | 0.0151 ± 0.0049 | 21.33 ± 5.59 |
| Control group | | 0.0147 ± 0.0037 | 21.40 ± 4.29 |
| Polysaccharide PS-C treated Group | 0.47 mg | 0.0117 ± 0.0041 | 29.67 ± 13.30 |
| Control group | | 0.0065 ± 0.0017 | 48.85 ± 11.52 |
| Extract A-treated group | 0.72 mg | 0.0173 ± 0.0035 | 18.19 ± 4.43 |
| Control group | | 0.0087 ± 0.0029 | 40.05 ± 18.82 |
| Extract B-treated group | 0.72 mg | 0.0178 ± 0.0032 | 16.88 ± 5.43 |
| Control group | | 0.0087 ± 0.0029 | 40.05 ± 18.82 |

Note
Each value of $K_2^{20}$ or $T\frac{1}{2}$ indicates mean value ± standard delivation value.

The half-value period in blood was shortened to about ½ by administering polysaccharide PS-A or PS-C extract A or B. Thus, it has been confirmed that the reticuloendothelial system is activated.

② Phagocytosis on *Staphylococcus aureus*:

A sample was administered subcutaneously to the back of each of 7- or 8-weeks-old female mice of the ICR/JCL stain having a body weight of about 27 g (each group consisting of 5 mice) once a day continuously for five days (5 times in total). PBS was given to a control group.

On the sixth day, the peritoneal cavity of each mouse of each group was washed with RPMI-1640 medium [G. E. Moore, The Journal of the American Medical Association, 199, pages 519-524 (1967)] (supplied by Nissui Seiyaku. Co., Ltd., Japan) to collect peritoneal exudate cells, and the collected cells were pooled respectively. The peritoneal exudate cells were washed one time with RPMI-1640 medium under centrifugation (1,000 r.p.m., 5 min.), and then suspended in 10% FBS-RPMI-1640 medium (culture medium formed by adding 10% of inactivated Fetal Bovine Serum to RPMI-1640 medium). The cell suspension was adjusted to $1 \times 10^6$ cells/ml by using Türk solution. Then 2 ml of the so obtained suspension was charged in a TD-15 bottle having 4 cover glass sheets attached thereto and culturing was conducted at 37° C. for 60 minutes in a 5% $CO_2$ incubator, and 0.1 ml of a suspension of *Staphylococcus aureus* 209P having a concentration of $4 \times 10^8$ cells/ml was added and culturing was further conducted for 20 minutes to effect phagocytosis. After culturing, the culture liquid was washed 3 times with Hanks' solution [J. H. Hanks and R. E. Wallace, Proceedings of the Society for Experimental Biology and Medicine, 71 196 (1949) (supplied by Nissui Seiyaku Co., Ltd., Japan)]. The macrophage-adhering cover glass sheets were fixed by methanol and subjected to Giemsa staining to obtain samples for counting the number of phagocytized bacteria and 200 macrophages were counted in each cover glass sheet microscopical observation with oil immersion objective (1000 to 2000 magnifications) to determine the phagocytosis ratio.

$$\text{Phagocytosis ratio} = \frac{\text{number of phagocytizing macrophages}}{200 \text{ (macrophages)}} \times 100 \ (\%)$$

Activation index =

$$\frac{\text{phagocytosis ratio of polysaccharide PS-A-treated group}}{\text{phagocytosis ratio of control group}}$$

The obtained results are shown in Table 14.

TABLE 14

Results of macrophage phagocytosis test

| Item | | Phagocytosis ratio (%) | Activation index |
|---|---|---|---|
| Control group | | 20.5 ± 3.0 | 1.00 |
| Polysaccharide PS-A-treated group | 0.2 mg/kg body wt./day | 34.3 ± 3.6 | 1.67 |
| | 1.0 mg/kg body wt./day | 33.5 ± 5.4 | 1.63 |

Note
Each value of phagocytosis ratio indicates mean value ± standard deviation value.

The phagocytosis ratio is improved by administering polysaccharide PS-A.

Thus, it has been confirmed that macrophage phagocytic activity is enhanced by polysaccharide PS-A.

③ Chemotaxis tests:

A sample of polysaccharide PS-A was administered subcutaneously to 7-weeks-old female mice of the ICR/JCL stranin having a body weight of about 27 g (each group consisting of 5 mice) once a day continuously for five days. PBS was given to a control group.

On the sixth day, peritoneal exudate cells were taken out, suspended in 10% FBS.RPMI-1640 medium and adjusted to a concentration of $1 \times 10^6$ cells/ml. The chemotaxis was examined by Boyden chamber method [Journal of Experimental Medicine; 115, 453 (1962)].

In the experiment, 0.2 ml of the RPMI-1640 medium containing 10% normal human serum was placed in a lower room and 0.2 ml of the thus prepared peritoneal exudate cell suspension was placed in an upper room and the incubation was effected by a 5% $CO_2$ incubator at 37° C. for 90 minutes.

A filter was taken out, fixed with methanol and subjected to Giemsa staining. The number of cells was counted by means of a microscope of 400 mangifications. The total number of the cells in five fields of view was counted and the average was determined. The results are shown in Table 15.

TABLE 15

Results of the chemotaxis tests

| Item | Dose | Number of chemotactic cells | Chemotaxis index |
|---|---|---|---|
| Control group | 0.2 (PBS)/mouse | 556.3 ± 52.8 | 1.00 |
| Polysaccharide PS-A-treated group | 0.04 mg/kg body wt./day | 968.0 ± 42.0 | 1.74 |
| | 0.2 mg/kg body wt./day | 996.0 ± 81.1 | 1.79 |
| | 1.0 mg/kg body wt./day | 1173.2 ± 71.5 | 2.11 |

Notes
1. Chemotaxis index = $\frac{\text{Number of chemotactic cells in polysaccharide PS-A-treated group}}{\text{Number of chemotactic cells in control group}}$
2. The number of chemotactic cells indicates the mean value ± standard deviation value.

By the administration of polysaccharide PS-A, the number of chemotactic cells was increased.

Namely, polysaccharide PS-A exhibited an effect of enhancing the chemotaxis of macrophages. From the above macrophage function tests ①-③, it is understood that polysaccharide PS-A remarkably enhances the macrophage function.

(2) Cellular immunity test

① Cytotoxicity test
(A) BC-47 cell:

(a) A sample of polysaccharide PS-A was administered subcutaneously to the back of each of 8-weeks-old female mice of BALB/c strain haing a body weight of about 22 g (each group consisting of 5 mice) once a day continuously for three days (3 times in total). On the first day of application of polysaccharide PS-A, BC-47 cells (the strain derived from the bladder cancer rat of the ACI strain and cultured in generations in a test tube) were injected to the intraperitoneal injection at a rate of $1 \times 10^7$ cells/mouse in both the polysaccharide PS-A-treated group and the control group to effect immunization. After 12 days from the immunization, the peritoneal cavity of each mouse of the above two groups and the normal mouse group was washed with RPMI-1640 medium to collect peritoneal exudate cells. The collected cells were pooled respectively, and the peritoneal cells were centrifugally washed 2 times with RPMI-1640 medium and 1 time with 20% FBS.RPMI-1640 medium and then suspended in the latter-mentioned medium. With respect to each group, the peritoneal exudate cell concentration was adjusted to $1.6 \times 10^5$ cells/ml, $3.2 \times 10^5$ cells/ml and $6.4 \times 10^5$ cells/ml by cell number counting using trypan blue.

(b) BC-47 cells cultured in a test tube were suspended in 20% FBS.RPMI-1640 medium to form a viable cell suspension having a concentration of $8 \times 10^4$ viable cells/ml.

(c) In a horizontal-bottom-type microplate for culturing of cells [Model N-1480 having 96 holes (wells); produced by NUNC Co., Ltd., Sweden], 0.1 ml/hole of the peritoneal exudate cell suspension ($1.6 \times 10^4$ cells) and 0.1 ml/hole of the test tube cultured BC-47 cell suspension ($8 \times 10^3$ cells) were subjected to culturing at 37° C. for 24 hours in a 5% $CO_2$ incubator, and then, 0.1 $\mu$Ci of $^3$H-thymidine was added to each hole and culturing was conducted under the same conditions for 24 hours. The operation was carried out in the same manner as above using the peritoneal exudate cell suspension ($3.2 \times 10^4$ cells and $6.4 \times 10^4$ cells, respectively).

(d) After completion of culturing, each hole was washed with PBS and BC-47 cells adhering and growing on the bottom face of the hole were treated by trypsin and collected on a filter paper by a cell harvester of minimush type (produced by Dynaetech Co., Ltd., England). The quantity of $^3$H uptake in the BC-47 cells in each hole (the number of $^3$H atoms destroyed per minute; dpm) was measured by a liquid scintillation counter (Model LSC-673; produced by Aloka Co., Ltd., Japan).

The propagation inhibition ratio was calculated according to the following formula:

$$(A-B)/A \times 100(\%)$$

wherein A indicates the mean value quantity ($\overline{M}$)(dpm/hole) of $^3$H uptake in BC-47 cells cultured singly and B denotes the mean value quantity ($\overline{M}$) (dpm/hole) of $^3$H uptake in BC-47 cells cultured together with peritoneal exudate cells of the normal mouse, the immunized mouse or the immunized and polysaccharide PS-A-treated mouse.

The activation index was calculated according to the following formula:

wherein C designates the propagation inhibition ratio of the immunized and polysaccharide PS-A-treated mouse and D stands for the propagation inhibition ratio of the immunized mouse (polysaccharide PS-A was not treated).

The obtained results are shown in Table 16.

TABLE 16
Results of cytotoxicity test

| Item | Quantity of $^3$H uptake (dpm) | | propagation inhibition ratio (%) | Activation index |
|---|---|---|---|---|
| BC-47 cells cultured singly | 44529.7 ± 988.3 | | 0 | — |
| Normal group | T:E = 1:2 | 39623.0 ± 1944.2 | 11.0 | — |
| | T:E = 1:4 | 37826.2 ± 1661.2 | 15.1 | |
| | T:E = 1:8 | 36726.0 ± 2212.0 | 17.5 | |
| Control group | T:E = 1:2 | 36788.6 ± 1968.7 | 17.4 | 1.00 |
| | T:E = 1:4 | 33248.1 ± 326.3 | 25.3 | 1.00 |
| | T:E = 1:8 | 24238.6 ± 950.4 | 45.6 | 1.00 |
| Polysaccharide PS-A-treated group | T:E = 1:2 | 28629.4 ± 671.4 | 35.7 | 2.05 |
| | T:E = 1:4 | 25497.6 ± 913.8 | 42.7 | 1.69 |
| | T:E = 1:8 | 18302.8 ± 245.5 | 58.9 | 1.29 |

Note
In the column of "Quantity of $^3$H uptake (dpm)", T:E = (BC-47 cell number):(peritoneal exudate cell number) and each value indicates mean value ± standard deviation value.

(B) P 815 Cells:

In the same manner as in (A), P 815 cells (the strain derived from masto-cytoma mouse of the DBA strain and cultured in generations in the abdomen of DBA mouse) were injected to the intraperitoneal injection at a rate of $5 \times 10^6$ cells/mouse. The spleen cells were taken out 7 days after the immunization and suspensions having concentrations of $2.5 \times 10^6$ cells/ml and $5.0 \times 10^6$ cells/ml were prepared. A suspension of P 815 viable cells was adjusted to a concentration of $2.0 \times 10^5$ cells/ml. The quantity of $^3$H uptake was measured by means of a liquid scintillation counter. The quantity of $^3$H uptake, propagation inhibition ratio and activation index are shown in Table 17. In the test, polysaccharide PS-A was administered subcutaneously to the back of each mouse in a dose of 0.2 mg/kg body weight once a day continuously for 3 days (3 times in total).

TABLE 17
Results of cytotoxicity test

| Item | Quantity of $^3$H uptake (dpm) | | Propagation inhibition ratio (%) | Activation index |
|---|---|---|---|---|
| P 815 cells cultured singly | 57674.7 ± 2075.6 | | 0 | — |
| Normal group | T:E = 1:12.5 | 50667.7 ± 1114.9 | 12.1 | — |
| | T:E = 1:25 | 41953.9 ± 867.8 | 27.3 | |
| Control group | T:E = 1:12.5 | 38320.5 ± 2930.1 | 33.6 | 1.00 |
| | T:E = 1:25 | 22609.6 ± 1324.9 | 60.8 | 1.00 |
| Polysaccharide PS-A-treated group | T:E = 1:12.5 | 23429.6 ± 1706.3 | 59.4 | 1.77 |
| | T:E = 1:25 | 10309.1 ± 1709.5 | 82.1 | 1.35 |

Note
In the column of "quantity of $^3$H uptake (dpm)" T:E = (P 815 cell number):(peritoneal exudate cell number) and each value indicates mean value ± standard deviation value.

Polysaccharide PS-A enhanced the effect of inhibiting the propagation of mouse effector cells such as (A) BC-47 cells and (B) P 815 cells.

② Blast transformation tests:

(A) Immunostimulation test on normal mice:

(a) Polysaccharide PS-A was administered to the back of each of 8-weeks-old female mice of the ICR/JCL stain having a body weight of about 28 g (each group consisting of 5 mice) by subcutaneous injection once a day continuously for five days (5 times in total). On the sixth day, mesenteric lymph node was teased out in RPMI-1640 medium. After allowing to stand for a while, a supernate was taken and centrifuged at 1200 r.p.m. for 5 minutes. The precipitates were taken and suspended in 20% FBS. RPMI-1640 medium. The suspension was adjusted to a concentration of $2 \times 10^6$ viable cells/ml according to a cell-number counting method using trypan blue. In control group, PBS was given to the back of each mouse by subcutaneous injection.

(b) In a horizontal-bottom-type microplate for culturing cells, 0.1 ml/hole of the cell suspension and 10 μl/hole of sample were charged. After the culture at 37° C. for 24 hours in a 5% $CO_2$ incubator, 0.1 μCi of $^3$H-thymidine wad added to each hole and the culture was continued under the same conditions for 24 hours.

(c) After completion of the culture, each hole was washed with PBS and the cells adhering to the bottom face of the hole were collected on a filter paper by means of a cell harvester. The quantity of $^3$H uptake (dpm) in the cells in each hole was measured by a liquid scintillation counter. The results are shown in Table 18.

TABLE 18
Results of immunostimulation test on normal mice

| Sample | Item | | Quantity of $^3$H uptake (dpm) | Activation index |
|---|---|---|---|---|
| PHA* (20 mg/ml) | Control group (PBS-treated group) | | 869.7 ± 61.4 | 1.00 |
| | Polysaccharide PS-A-treated group | 0.04 mg/kg body wt./day | 4678.3 ± 872.2 | 5.38 |
| | | 0.2 mg/kg body wt./day | 5758.9 ± 149.2 | 6.62 |
| | | 1.0 mg/kg body wt./day | 5962.7 ± 438.8 | 6.86 |
| LPS** (50 mg/ml) | Control group (PBS-treated group) | | 178.4 ± 55.6 | 1.00 |
| | Polysaccharide PS-A-treated | 0.04 mg/kg body wt./day | 447.1 ± 72.2 | 2.51 |
| | | 0.2 mg/kg body wt./day | 467.3 ± 43.4 | 2.62 |
| | | 1.0 mg/kg body wt./day | 675.6 ± 71.5 | 3.79 |

Note
1. *PHA (phytohemagglutinin): A mitogen of Difco Laboratory Co. (U.S.A.) obtained from kidney beans. Effective on T-cells.
2. **LPS (Lipopolysaccharide) A mitogen of Difco Laboratory Co. (U.S.A.) obtained from gram-negative bacteria. Effective on B-cells.
3. Quantity of $^3$H uptake is shown by the mean value ± standard deviation value.
4. Activation index = $\dfrac{\text{Quantity of }^3\text{H uptake in polysaccharide PS-A-treated group}}{\text{Quantity of }^3\text{H uptake in control group}}$ (B) Immunostimulation test on mice in the immunosuppressive state:

(a) 31.3 mg of cyclophosphamide was intraperitoneally injected each of 8-weeks-old female mice of the ICR/JCL strain having a body weight of about 28 g (each group consisting of 3 mice). On the same day, the subcutaneous injection of polysaccharide PS-A into the back of the mouse was started. The injection was continued for 4 days (once a day). On the fifth day, mesenteric lymph node was teased out in RPMI-1640 medium. After allowing to stand for a while, a supernate was taken and centrifuged at 1200 r.p.m. for 5 minutes. The precipitates were taken and suspended in 20% FBS.RPMI-1640 medium. The suspension was adjusted to a concentration of $2 \times 10^6$ viable cells/ml according to a cell-number counting method using trypan blue. In control group, PBS was given to the back of each mouse by subcutaneous injection. Thereafter, the quantity of $^3H$ uptake (dpm) was measured in the same manner as in items (b) and (c) in the immunostimulation test on normal mice (A). The results are shown in Table 19.

TABLE 19

Results of immunostimulation test
on mice in the immunosuppressive state

| Sample | Item | | Quantity of $^3H$ uptake (dpm) | Activation index |
|---|---|---|---|---|
| PHA (20 mg/ml) | Normal group* | | 8034.8 ± 612.5 | — |
| | Control group (PBS-treated group) | | 2797.0 ± 475.1 | 1.00 |
| | Polysaccharide PS-A-treated group | 0.2 mg/kg body wt./day | 13404.7 ± 1852.1 | 4.79 |
| | | 1.0 mg/kg body wt./day | 13573.7 ± 516.1 | 4.85 |
| | | 5.0 mg/kg body wt.day | 14970.2 ± 383.6 | 5.35 |
| LPS (50 mg/ml) | Normal group* | | 913.6 ± 83.5 | — |
| | Control group (PBS-treated group) | | 678.6 ± 75.6 | 1.00 |
| | Polysaccharide PS-A-treated group | 0.2 mg/kg body wt./day | 1584.5 ± 100.1 | 2.34 |
| | | 1.0 mg/kg body wt./day | 2081.3 ± 313.1 | 3.07 |
| | | 5.0 mg/kg body wt./day | 2922.1 ± 397.5 | 4.31 |

Note
*Normal group: Group of mice to which PSB was injected (cyclophosphamide was not injected), i.e., group of mice in normal state.

It has been confirmed that by the administration of polysaccharide PS-A, the quantity of $^3H$ uptake is increased in the normal mice (A) and restored to a value equal to or higher than that of the normal mice in the mice in the innumosuppressive state (B).

Namely, by the administration of polysaccharide PS-A, the cellular blast transformation by the mitogen is accelerated and the cellular immunity is enhanced.

From the above tests ① and ②, it has been confirmed that polysaccharide PS-A remarkably enhances the cellular immunity. It is apparent from the above macrophage function test (1) and cellular innunity test (2) that polysaccharide PS-A exhibited the immunosimulating effects.

(III) Acute toxicity test

The acute toxicity was tested according to Lichfield-Wilcoxon method [J. Pharm. Exp. Therm., 96, 99 (1949)] by using male mice of the ICR/JCL strain.

The results are shown in Table 20.

TABLE 20

| | Results of acute toxicity test | |
|---|---|---|
| Item | Peroral (mg/kg body wt./day) | Intravenous (mg/kg body wt./day) |
| Polysaccharide PS-A | more than 3,000 | more than 400 |
| Polysaccharide PS-B | more than 3,000 | more than 600 |
| Polysaccharide PS-C | more than 3,000 | more than 400 |
| Extract A | more than 3,000 | more than 600 |
| Extract B | more than 3,000 | more than 600 |

It has been confirmed that polysaccharides PS-A, PS-B and PS-C and extracts A and B have low toxicity.

From the results of tests (I)–(III), it has been confirmed that polysaccharide PS-A having the low toxicity and the phylactic effect can be used alone or in combination with antibiotics to form a phylactic agent.

Polysaccharide PS-A having the immunostimulating effect as well can be used for remedy of living animals.

Though the mechanisms of the effects of polysaccharide PS-A have not been fully elucidated, it has been concluded from the immunostimulating effect and phylactic effect that polysaccharide PS-A remarkably improves the vital defense mechanisms.

From this fact, the use of polysaccharide PS-A as a carcinostatic agent or an agent for preventing the metastasis of cancer and so on can be expected.

Polysaccharide PS-A may be administered to human body orally, by injection (intravenously, subcutaneously or intramuscularly) or in any other manner.

When polysaccharide PS-A is in the form of solid preparations for oral administration, the preparations may be tablets, granules, powders, capsules or the like. The preparations may contain additives, for example, an excipient such as a sacchride or cellulose preparation, a binder such as starch paste or methyl cellulose, a filler, a disintegrator and so on, all being ones usually used in the manufacture of medical preparations. In case polysaccharide PS-A is employed as oral liquid preparations, they may be of any form selected from aqueous preparations for internal use, suspensions, emulsions, syrups, etc., and further they may be in the form of dried products which are dissolved prior to the use.

When polysaccharide PS-A is orally administered to adults, they may be employed in a dose of 0.1 ~ 2 mg/kg per day. Here, of course, the dose may be increased or decreased appropriately depending on the conditions of disease, the age of the patient, the form of the preparation administered, etc.

Polysaccharide PS-A may be injected in the form of aqueous solutions, spensions or oily or aqueous emulsions, but usually the injections are prepared by dissolving or spending them in aqueous liquid media such as sterile water of physiologicl saline solutions. If necessary, conventionally used dissolving agents, stabilizers, preservatives, additives for preparing isotonic solutions, etc. may be added to the injections.

The thus obtained injection preparations are administered intravenously, intramuscularly, subcutaneously or in any other appropriate manner. When polysaccharide PS-A is administered to adults parenterally, they may contain 0.005 to 0.5 mg/kg per day. Of course, this dose level is increased or decreased appropriately depending on the conditions of disease, the age of the patient, the form of the preparation administered and the method of administration.

The machines and tools used in the present invention were as follows:
  (i) Elementary analysis: Yanagimoto MT-2 Type (produced by Yanagimoto Co., Ltd., Japan)
  (ii) Decomposition Point: Melting Point Determinator Identi-scope Type (produced by Mitamura Riken Co., Ltd., Japan)
  (iii) pH: Toadenpa HM-5B Type (Toadenpa Co., Ltd., Japan)
  (iv) Specific rotatory power: Perkin-Elmer 241 Type (produced by Perkin-Elmer Co., Ltd., U.S.A.)
  (v) Infrared absorption spectrum: Hitachi 260-10 Type (produced by Hitachi Co., Ltd., Japan)
  (vi) Ultraviolet absorption spectrum: Hitachi 124 Type Spectrophotometer (produced by Hitachi Co., Ltd., Japan)
  (vii) Ultracentrifugation: Hitachi 55P-7 (RPS 56T Rotor) (produced by Hitachi Co., Ltd., Japan)
  (viii) Electrophoresis: Joko PAV-200 (produced by Joko Co., Ltd., Japan)
  (ix) Sephadex G: Polysaccharide dextran reacted with epichlorohydrin for three-dementional cross-linking into network (produced by Pharmacia Fine Chemical Co., Ltd., Sweden). Particles used for the present invention were as follows:

| Type of gel | Minimum treatment time for swelling (hour) At 20-25° | Minimum treatment time for swelling (hour) At 90-100° | Bed volume of swelled gel ml/g dry gel | Optimum area of molecular weight of polysaccharides | Minimum exclusion limit of molecular weight of polysaccharides ($K_d = 0$) |
|---|---|---|---|---|---|
| G-100 | 72 | 5 | 15–20 | 1,000–50,000 | 100,000 |
| G-150 | 72 | 5 | 20–30 | 1,000–100,000 | 150,000 |
| G-200 | 72 | 5 | 30–40 | 1,000–150,000 | 200,000 |

(x) Barrenworts used were obtained from Matsuura Yakugyo Co., Ltd., in Nagoya, Japan.

Figure 1:
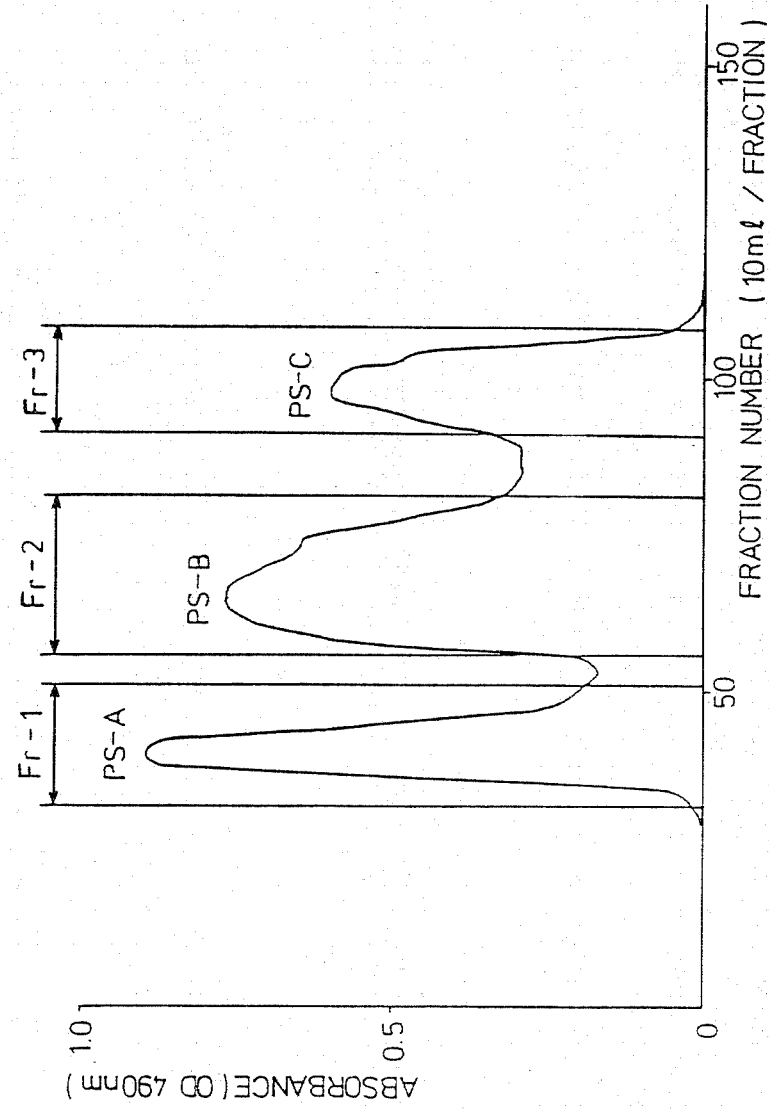
FIG. 1 shows the chromatogram for extract A.
Figure 2:
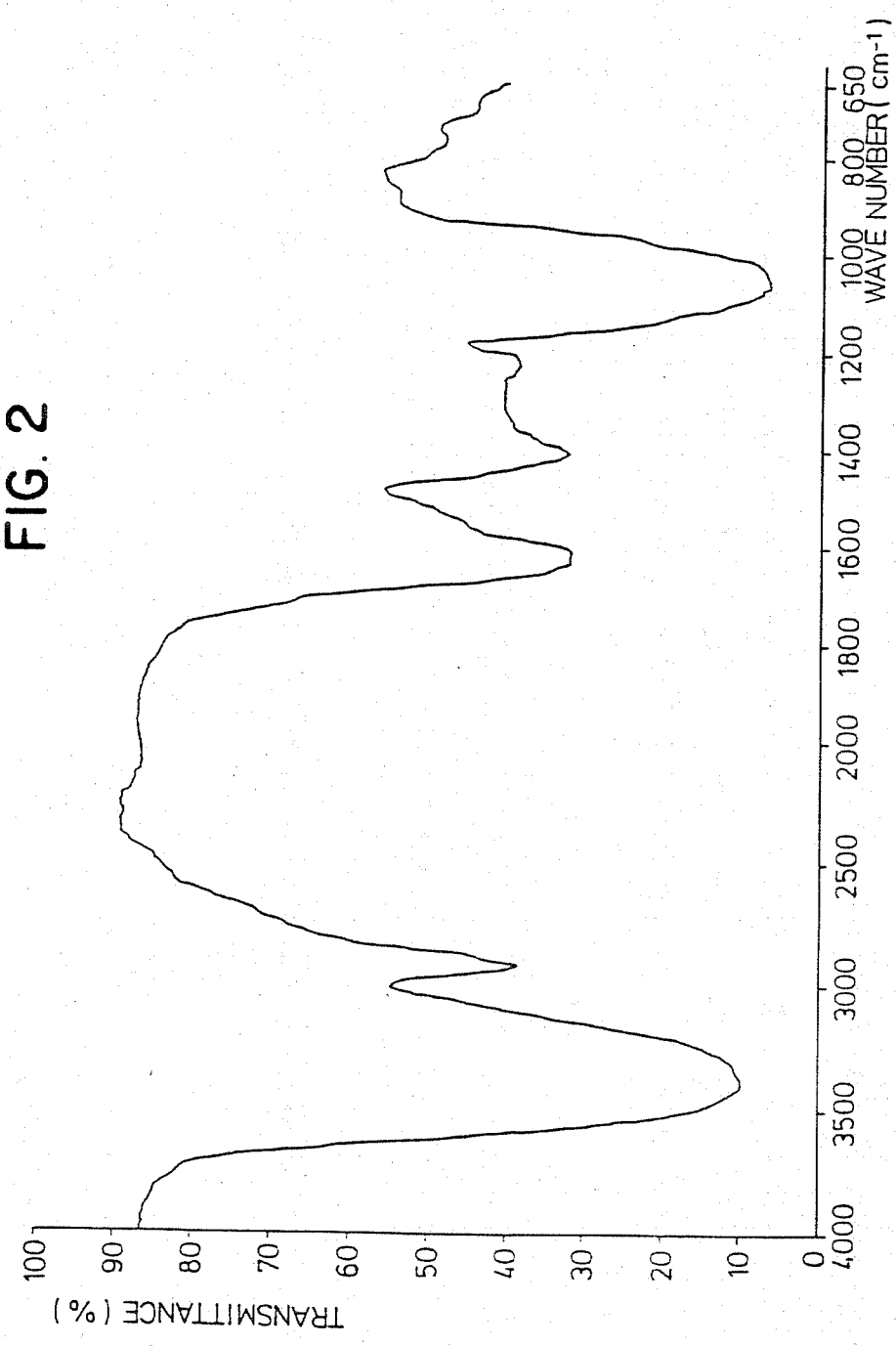
FIGS. 2 to 6 show the infrared absorption spectrums for polysaccharides PS-A, PS-B and PS-C and extracts A and B, respectively.
Figure 3:
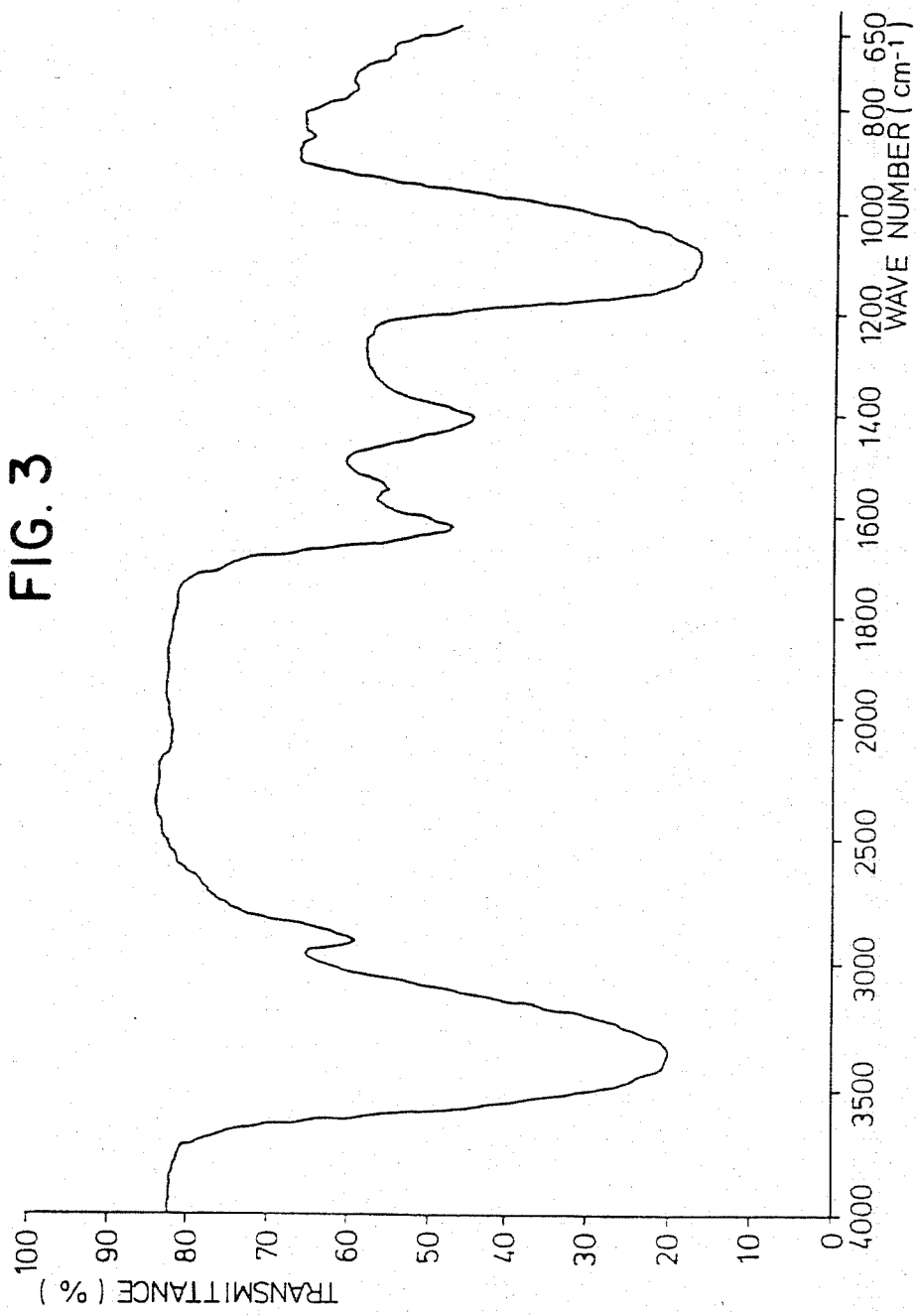
Figure 4:
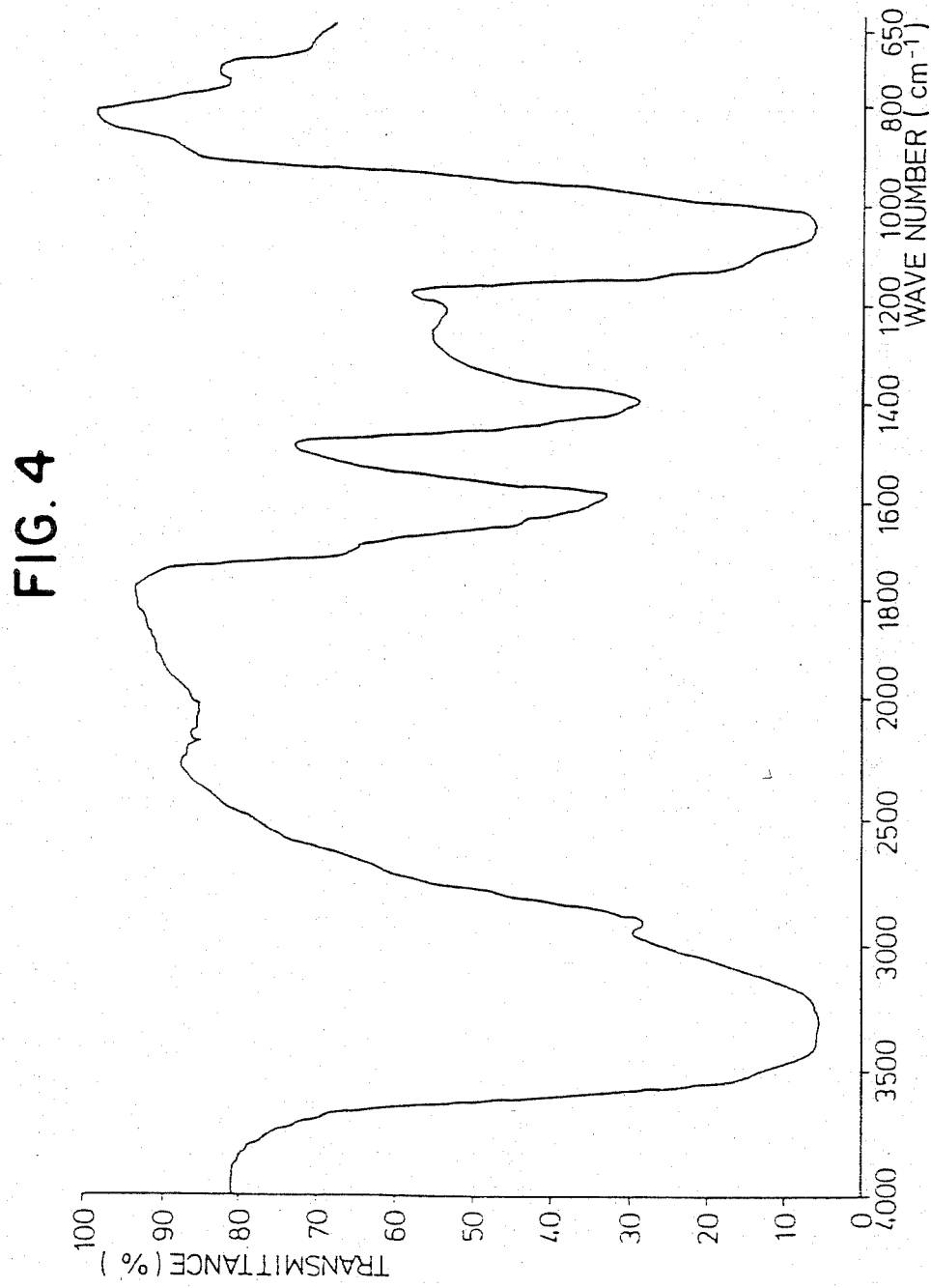
Figure 5:
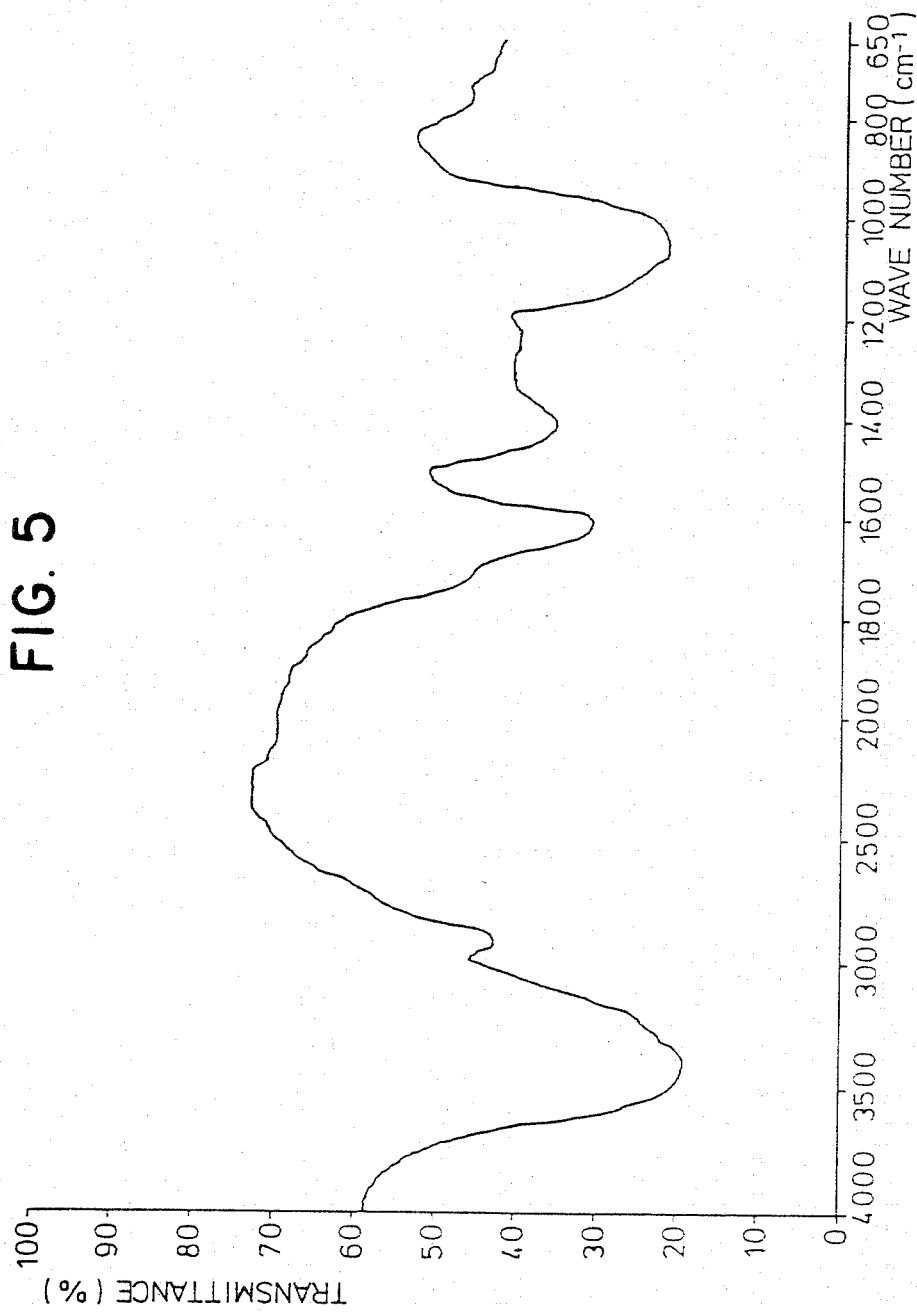
Figure 6:
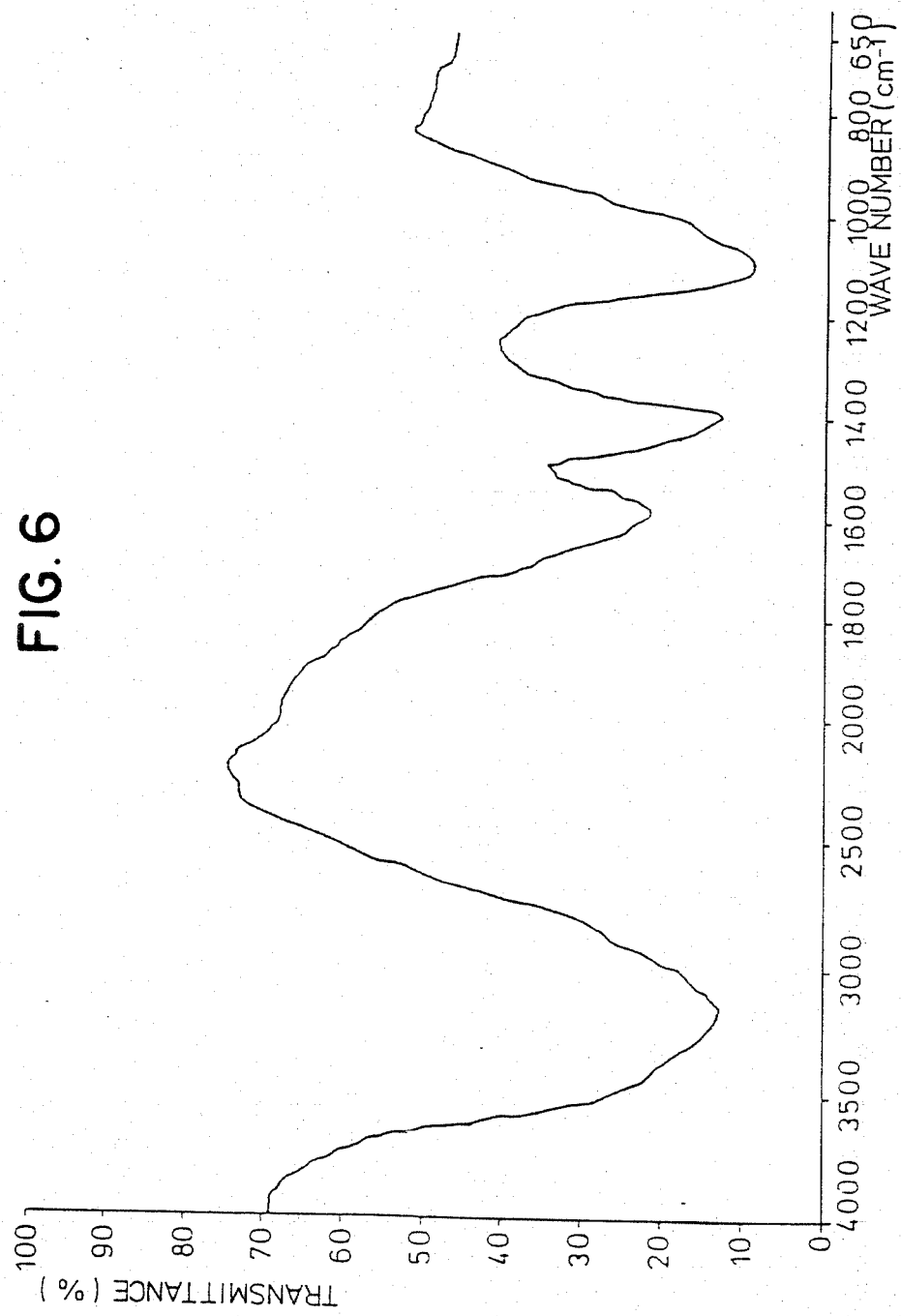

The present invention will now be described in detail with reference to the following preparation examples that by no means limit the scope of the present invention.

PREPARATION EXAMPLE 1

15 l of 50% ethanol (V/V) was added to 2 kg of finely devided, commercially available barrenwort (*Epimedium koreanum*, Nak. preduced in Korea) and the extraction was carried out under heating at 50° C. on a water bath for 6 hours using a reflux condenser. After the extraction, the mixture was filtered while it was still warm and the residue was further extracted 3 times in the same manner as above, using 15 l of 50% ethanol (V/V) each time. All the filtrates were combined and then concentrated at 45° C. under reduced pressure to obtain 10 l of an aqueous extract. The extract was charged in a separating funnel. 5 l of ethyl acetate was added thereto and the mixture was shaken sufficiently. Only the aqueous layer was recovered. The aqueous layer was further extracted 3 times in the same manner as above using 5 l of ethyl acetate each time. The aqueous layer was concentrated under reduced pressure and the residual ethyl acetate was distilled out. The residue was filtered. 30 l of ethanol was added to the filtrate and the mixture was stirred and left overnight. A precipitate thus formed was filtered. The precipitate was washed with 200 ml of ethanol and poured in 2 l of water. 8 l of ethanol was added thereto and the thus formed precipitate was filtered out. The precipitate was dried under reduced pressure to obtain 20 g of an extract. The extract was further subjected to the extraction with 1 l of water and filtered. The filtrate was concentrated to dryness under reduced pressure to obtain 16 g of an extract in the form of dark brown powder.

1 l of 0.02 Mol aqueous sodium sulfate solution was added to 16 g of the extract. The mixture was stirred under heating at 40° C. and then filtered while it was still warm. 100 ml of 10% aqueous cetyltrimethylammonium bromide solution was added to the filtrate under heating at 30°–40° C. The mixture was kept at 37° C. overnight and then centrifuged (3,000 r.p.m., 10 minutes) to obtain 1 l of a supernate. 3 l of ethanol was added to the supernate and the resulting precipitate (3.0 g) was filtered out. 1 l of water was added to 3.0 g of the precipitate and the mixture was stirred under heating at 40° C. and then filtered while it was warm. The filtrate was further filtered through Millipore Filter AP 20 (142 mm diameter; produced by Nippon Millipore Limited, Japan) and Millipore Membrane Filter HA (142 mm diameter, 0.45 μm pore diameter; produced by Nippon Millipore Limited, Japan). The filtrate was then subjected to the ultrafiltration through Millipore Pellicon Ultrafiltration Membrane PSAC (nominal molecular weight ultrafiltration value of 1,000; produced ty Nippon Millipore Limited, Japan) and the filtrate was removed. Then, 500 ml of water was added to the residue and the thus diluted residue was again subjected to the ultrafiltration. This operation was repeated three times. The filtration residue was taken and diluted with water to a volume of 250 ml. 1 l of ethanol was added thereto to obtain 2.0 g of extract A as a precipitate.

2.0 g of extract A was dissolved in 20 ml of water and treated with a Sephadex G-150 column (50 mm diameter ×600 mm length; produced by Pharmcia Fine Chemical Co., Ltd., Sweden). By the elution with 10 ml of water each time, 150 fractions were obtained. A part (about 0.2 ml) of each fraction was color-developed with phenol-sulfuric acid method successively and absorbance at 490 nm (OD) was measured. Fractions corresponding to Fr-1 in FIG. 1 (elution fractions Nos. 30–51) were selectively collected, concentrated under reduced pressure and then freeze-dried to obtain 600 mg of polysaccharide PS-A. The product had the physicochemical properties shown above.

PREPARATION EXAMPLE 2

15 l of 50% ethanol (V/V) was added to 2 kg of finely devided, commercially available barrenwort (*Epimedium koreanum*, Nak. produced in Korea) and the extraction was carried out under heating at 50° C. on a water bath for 6 hours using a reflux condenser. After the extraction, the mixture was filtered while it was still warm and the residue was further extracted 3 times in the same manner as above, using 15 l of 50% ethanol (V/V) each time. All the filtrates were combined and then concentrated at 45° C. under reduced pressure to obtain 10 l of an aqueous extract. The extract was charged in a separating funnel. 5 l of ethyl acetate was added thereto and the mixture was shaken sufficiently. Only the aqueous layer was recovered. The aqueous layer was further extracted 3 times in the same manner as above using 5 l of ethyl acetate each time. The aqueous layer was concentrated under reduced pressure and the residual ethyl acetate was distilled out. The residue was diltered. 30 l of ethanol was added to the filtrate and the mixture was stirred and left overnight. A precipitate thus formed was filtered out. The precipitate was washed with 200 ml of ethanol and poured in 2 l of water. 8 l of ethanol was added thereto and the thus formed precipitate was filtered out. The precipitate was dried under reduced pressure to obtain 20 g of an extract. The extract was further subjected to the extraction with 1 l of water and filtered. The filtrate was concentrated to dryness under reduced pressure to obtain 16 g of an extract in the form of dark brown powder.

1 l of 0.02 Mol aqueous sodium sulfate solution was added to 16 g of the extract. The mixture was stirred under heating at 40° C. and then filtered while it was still warm. 100 ml of 10% aqueous cetyltrimethylammonium bromide solution was added to the filtrate under heating at 30°–40° C. The mixture was kept at 37° C. overnight and centrifuged (3,000 r.p.m., 10 minutes) to obtain 1 l of a supernate. 3 l of ethanol was added to the supernate and the resulting precipitate (3.0 g) was filtered out. 1 l of water was added to 3.0 g of the precipitate and the mixture was stirred under heating at 40° C. and then filtered while it was warm. The filtrate was further filtered through Millipore Filter AP 20 (142 mm diameter; produced by Nippon Millipore Limited, Japan) and Millipore Membrane Filter HA (142 mm diameter, 0.45 μm pore diameter; produced by Nippon Millipore Limited, Japan). The filtrate was then subjected to the ultrafiltration through Millipore Pellicon Ultrafiltration Membrane PSAC (nominal molecular weight ultrafiltration value of 1,000; produced by Nippon Millipore Limited, Japan) and the filtrate was removed. Then, 500 ml of water was added to the residue and the thus diluted residue was again subjected to the ultrafiltration. This operation was repeated three times. The filtration residue was taken and diluted with water to a volume of 250 ml. 1 l of ethanol was added thereto to obtain 2.0 g of extract A as a precipitate.

500 ml of water was added to extract A and the mixture was stirred under heating at about 40° C. to obtain a solution. The solution was filtered while it was still warm. The thus obtained filtrate was subjected to the column chromatography (45 mm column diameter, 400 mm length) using Polyamide C-200 (produced by Wako Junyaku Co., Ltd., Japan). After the elution with 2 l of water, the fractions thus eluted out with water which exhibited positive reactivity in α-naphthol reaction were concentrated to dryness under reduced pressure to obtain 1.0 g of polysaccharide PS-B having the physicochemical properties shown above. Then, water used for the elution was replaced with 3 l of 1.4% aqueous ammonia solution to obtain fractions which exhibited positive reactivity in α-naphthol reaction. The fractions were concentrated to dryness under reduced pressure to obtain 0.8 g of extract B having the physicochemical properties shown above.

0.8 g of extract B was dissolved in 20 ml of water and subjected to the elution by means of a Sephadex G-150 column with 10 ml of water each time. A part (about 0.2 ml) of each fraction was color-developed with phenolsulfuric acid method successively and absorbance at 490 nm (OD) was measured. The fractions which were color-developed in the initial stage with phenol-sulfuric acid were selectively collected, concentrated under reduced pressure and then freeze-dried to obtain 200 mg of polysaccharide PS-A. The product had the physicochemical properties shown above.

EXAMPLE 1

10 mg of the polysaccharide obtained in Preparation Example 2 was dissolved in 100 ml of physiological saline solution. 5 ml of the solution was charged in an ampoule and sealed. The ampoules thus prepared were sterilized by an ordinary method to obtain injections of the extract of the present invention.

EXAMPLE 2

0.5 mg of the polysaccharide obtained in Preparation Example 2 was charged in a vial. This product is to be dissolved in sterilized water at the time of use to obtain an injection.

EXAMPLE 3

1.0 g of the polysaccharide obtained in Preparation Example 1 was blended with 140 g of crystallized cellulose, 5 g of magnesium stearate and 4 g of talc in a twin-cylinder mixer for 5 minutes. The resulting powdery mixture was shaped into tablets by means of a pestle having a rounded edge, a flat face and a diameter of 8.0 mm by direct tableting method to obtain 1,000 tablets having a diameter of 8.0 mm, thickness of 3.0 mm and weight of 150 mg.

EXAMPLE 4

200 mg of the polysaccharide obtained in above Preparation Example 1 was blended with 99.8 g of lactose in a twin-cylinder mixer for 5 minutes. Portions (2 g) of the mixture were charged in aluminum tape packs the three sides of which had been sealed to obtain the powdery product.

EXAMPLE 5

1.0 g of the polysaccharide obtained in Preparation Example 1 was blended with 50 g of calcium hydrogenphosphate, 2 g of aluminum sillicate, 95 g of crystalline cellulose and 2 g of magnesium stearate in a twin-cylinder mixer for 5 minutes. The mixture was further mixed well by passing the same through a sieve. By an ordinary method, 1,000 capsules each containing 150 mg of the mixture were obtained.

CAPABILITY OF EXPLOITATION IN INDUSTRY

As described above in detail, the polysaccharide PS-A is obtained from easily available plants belonging to the genus Epimedium. Thus, the polysaccharide PS-A can be produced relatively easily on a large scale by the extraction and isolation from the above-mentioned plants according to the process of the present invention. The polysaccharide PS-A exhibits remarkable phylactic and immunostimulating effects and, therefore, excellent clinical effects thereof are expected when it is used as a medicine. The phylactic agent or the immunostimulating agent containing the polysaccharide PS-A can be obtained easily by mixing the same with a pharmaceutically allowable diluent or carrier and it can be administered to human bodies easily.

We claim:

1. A polysaccharide PS-A obtained from barrenwort derived from plants belonging to the genus Epimedium and having the following physicochemical properties (1) through (12):
   (1) Elementary analysis: C=40.92, H=6.17, Ash=very small;
   (2) Molecular weight: 75,000±25,000 (average molecular weight);
   (3) Decomposition point: 205° C.;
   (4) pH: 7.0(solution of 100 mg. of PS-A in 50 ml. of water);
   (5) Specific rotatory power: $[\alpha]_D^{19}=23.6°$ (in $H_2O$, c=0.527);
   (6) Infrared absorption spectrum: $\nu_{max}^{KBr}$ ($cm^{-1}$)/3400, 2900, 1620, 1400, 1230, 1060;
   (7) Ultraviolet absorption spectrum: Maximum absorption is not recognized in the range of 240-400 nm.;
   (8) Outward form: White or faint brown, amorphous powder;
   (9) Solubility:
       (a) Soluble in water;
       (b) Insoluble in methanol, ethanol, acetone, ethyl acetate, diethyl ether, hexane or chloroform;
   (10) Color reactions:
       Positive to the following reactions: (a) anthronesulfuric acid reaction, (b) Molisch's reaction, (c) skatol reaction and (d) Bial's reaction; and
       Negative to the following reactions: (a) ninhydrin reaction, (b) 2,4-DNP reaction, (c) Selivanoff's reaction, (d) naphthoresorcinol reaction and (e) carbazolsulfuric acid reaction;
   (11) Component sugars: Arabinose and galactose;
   (12) Homogeneity: Homogeneity is proved according to the ultracentrifugation, electrophoresis and gel filtration.

2. A polysaccharide PS-A according to claim 1, wherein said barrenwort is derived from *Epimedium koreanum* Nak.

3. A polysaccharide PS-A according to claim 1, which is obtained by the steps of extraction of said barrenwort using 50% ethanol (V/V), removal of portions soluble in ethyl acetate, addition of ethanol for precipitation, removal of cetyltrimethylammonium compounds, ultrafiltration and gel filtration.

4. A phylactic and immunostimulating agent comprising as an effective component said polysaccharide PS-A according to claim 1 and a pharmaceutically acceptable excipient.

5. A phylactic and immunostimulating agent according to claim 4, wherein said barrenwort is derived from *Epimedium koreanum* Nak.

* * * * *